(12) United States Patent
Wang et al.

(10) Patent No.: US 11,236,140 B2
(45) Date of Patent: *Feb. 1, 2022

(54) INTERLEUKIN 15 FUSION PROTEIN FOR TUMOR TARGETING THERAPY

(71) Applicant: BJ Bioscience Inc., Hangzhou (CN)

(72) Inventors: Zhong Wang, Guangzhou (CN); Qing Li, Guangzhou (CN)

(73) Assignee: BJ Bioscience Inc., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/798,269

(22) Filed: Feb. 21, 2020

(65) Prior Publication Data
US 2020/0270323 A1 Aug. 27, 2020

Related U.S. Application Data

(63) Continuation of application No. 15/747,029, filed as application No. PCT/CN2016/088158 on Jul. 1, 2016, now Pat. No. 10,611,812.

(30) Foreign Application Priority Data

Jul. 2, 2015 (CN) .......................... 201510378781.2

(51) Int. Cl.
| | |
|---|---|
| C07K 14/54 | (2006.01) |
| C07K 14/71 | (2006.01) |
| C07K 19/00 | (2006.01) |
| A61K 38/20 | (2006.01) |
| A61K 38/17 | (2006.01) |
| A61K 47/68 | (2017.01) |
| A61P 35/04 | (2006.01) |
| C07K 14/715 | (2006.01) |
| A61K 38/08 | (2019.01) |
| C07K 7/06 | (2006.01) |
| A61P 35/00 | (2006.01) |
| C12N 15/62 | (2006.01) |
| C12N 15/64 | (2006.01) |
| C12N 15/63 | (2006.01) |
| C12N 15/11 | (2006.01) |

(52) U.S. Cl.
CPC .......... *C07K 14/5443* (2013.01); *A61K 38/08* (2013.01); *A61K 38/1793* (2013.01); *A61K 38/20* (2013.01); *A61P 35/00* (2018.01); *A61P 35/04* (2018.01); *C07K 7/06* (2013.01); *C07K 14/7155* (2013.01); *C07K 19/00* (2013.01); *C07K 2319/30* (2013.01); *C07K 2319/70* (2013.01); *C12N 15/11* (2013.01); *C12N 15/62* (2013.01); *C12N 15/63* (2013.01); *C12N 15/64* (2013.01)

(58) Field of Classification Search
CPC .......... C07K 14/5433; C07K 14/7155; C07K 19/00; C07K 2319/035; C07K 2319/33

See application file for complete search history.

(56) References Cited

U.S. PATENT DOCUMENTS

| 10,358,477 B2 | 7/2019 | Jacques et al. |
| 2005/0025771 A1 | 2/2005 | Wagner et al. |
| 2014/0134128 A1 | 5/2014 | Wong et al. |

FOREIGN PATENT DOCUMENTS

| CN | 101824406 | 9/2010 |
| CN | 102488890 | 6/2012 |
| CN | 103370339 | 10/2013 |
| CN | 103974711 | 8/2014 |
| CN | 107636015 | 1/2018 |
| WO | WO-2012175222 | 12/2012 |

OTHER PUBLICATIONS

Anderson et al, 1995. The Journal of Biological Chemistry. 270(50): 29862-29869.*
Bernard et al., Identification of an interleukin-15 alpha receptor binding site on human interleukin-15, J. Biol. Chem, published online Mar. 23, 2004. (45 pages).
Pfaff et al., Selective recognition of Cyclic RGD Peptides of NMR Defined Conformation by αIIβ3, αVβ3, and α5β1 Integrins, Journal of Biological Chemistry, vol. 269, No. 32, Issue of Aug. 12, p. 20233-20238, 1994.
Australian Second Office Action for Australian Patent Application No. 2016288484 dated May 13, 2019 (5 pages).
Bessard et al., "High antitumor activity of RLI, an interleukin015 (IL-15)-IL-15 receptor α fusion protein, in metastatic melanoma and colorectal cancer", Mol Cancer Ther 2009; 8(9), Sep. 2009, pp. 2736-2745.
Canadian Office Action dated Jan. 25, 2019 for Canadian Patent Application No. 2,993, 891 (3 pages).
Chen et al., "A targeted IL-15 fusion protein with potent anti-tumor activity," Cancer Biology & Therapy, vol. 16, Issue 9, Sep. 2015, pp. 1415-1421.

(Continued)

*Primary Examiner* — Zachary C Howard
(74) *Attorney, Agent, or Firm* — Sheppard Mullin Richter & Hampton LLP (57) ABSTRACT

Disclosed is a tumor-targeting fusion protein comprising at least (i) a IL-15 peptide or a variant or functional fragment thereof, (ii) a IL-15Rα polypeptide or a variant or functional fragment thereof, (iii) a Fc domain or a variant or functional fragment thereof, and (iv) a RGD polypeptide or a variant thereof. The fusion protein is preferably configured as RGD polypeptide-Fc domain-IL-15 polypeptide-IL-15Rα polypeptide. The tumor-targeting fusion proteins provided herein improves the anti-tumor effects of IL-15 and prolongs the half-life of IL-15, while targeting tumor sites and acting upon tumor cells. In addition, the fusion proteins are capable of being expressed at high efficiency and purified. The high efficiency of anti-tumor activity enables the fusion proteins to be an excellent candidate for tumor immunotherapy.

7 Claims, 7 Drawing Sheets
Specification includes a Sequence Listing.

(56) References Cited

OTHER PUBLICATIONS

Chinese First Office Action for Chinese Patent Application No. 201510378781.2 dated Mar. 21, 2019 (4 pages).
Danhier et al., "RGD-Based Straegies to Target Alpha(v) Beta(3) Integrin in Cancer Therapy and Diagnosis", Molecular Pharmaceutics, 2012, vol. 9, pp. 2961-2973.
European Search Report for EP Patent Application No. 168172773.3 dated Dec. 4, 2018 (11 pages).
Examination Report for AU 2016288484 dated Jul. 4, 2018 (3 pages).
International Search Report and Written Opinion of PCT/CN2016/088158 dated Oct. 10, 2016 with English Translation (16 pages).
Mortier et al., "Soluble Interleukin-15 Receptor α (IL-15(Rα)-sushi as a Selective and Potent Agonist of IL-15 Action through IL-15Rβ/γ," The Journal of Biological Chemistry vol. 281, No. 3, Jan. 20, 2006, pp. 1612-1619.
Robinson et al., "The Potential and Promise of IL-15 in Immuno-Oncogenic Therapies", Accepted Manuscript, Immunology Letters, (2017) (25 pages).
Stoklasek, "Combined IL-15/IL-15Ra Immunotherapy Maximizes IL-15 Activity In Vivo," J Immunol, Nov. 1, 2016, 177(9), 6072-6080.
Vincent et al., "Tumor targeting of the IL-15 superagonist RLI by an anti-GD2 antibody strongly enhances its antitumor potency," International Journal of Cancer, (2013) vol. 133, pp. 757-766.
Yu, "Progress in the Research of Cytokine Recombinant Chimeric Proteins," Chin J Cancer Biother, Jun. 2004, 11(2), 148-150.

\* cited by examiner

```
                              SEQUENCE LISTING

<160> NUMBER OF SEQ ID NOS: 13

<210> SEQ ID NO 1
<211> LENGTH: 227
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 2
<211> LENGTH: 77
<212> TYPE: PRT
<213> ORGANISM: Homo sapiens

<400> SEQUENCE: 2

Pro Pro Pro Met Ser Val Glu His Ala Asp Ile Trp Val Lys Ser Tyr
1               5                   10                  15

Ser Leu Tyr Ser Arg Glu Arg Tyr Ile Cys Asn Ser Gly Phe Lys Arg
                20                  25                  30

Lys Ala Gly Thr Ser Ser Leu Thr Glu Cys Val Leu Asn Lys Ala Thr
            35                  40                  45
```

```
Asn Val Ala His Trp Thr Thr Pro Ser Leu Lys Cys Ile Arg Asp Pro
 50                  55                  60

Ala Leu Val His Gln Arg Pro Ala Pro Pro Ser Thr Val
 65                  70                  75

<210> SEQ ID NO 3
<211> LENGTH: 114
<212> TYPE: PRT
<213> ORGANISM: Homo sapiens

<400> SEQUENCE: 3

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 4
<211> LENGTH: 11
<212> TYPE: PRT
<213> ORGANISM: Artificial Sequence
<220> FEATURE:
<223> OTHER INFORMATION: RGD polypeptide

<400> SEQUENCE: 4

Ala Cys Asp Cys Arg Gly Asp Cys Phe Cys Gly
 1               5                  10

<210> SEQ ID NO 5
<211> LENGTH: 459
<212> TYPE: PRT
<213> ORGANISM: Artificial Sequence
<220> FEATURE:
<223> OTHER INFORMATION: Tumour-targeting fusion protein

<400> SEQUENCE: 5

Ala Cys Asp Cys Arg Gly Asp Cys Phe Cys Gly Gly Gly Gly Ser
 1               5                  10                  15

Asp Lys Thr His Thr Cys Pro Pro Cys Pro Ala Pro Glu Leu Leu Gly
                 20                  25                  30

Gly Pro Ser Val Phe Leu Phe Pro Pro Lys Pro Lys Asp Thr Leu Met
             35                  40                  45

Ile Ser Arg Thr Pro Glu Val Thr Cys Val Val Val Asp Val Ser His
 50                  55                  60

Glu Asp Pro Glu Val Lys Phe Asn Trp Tyr Val Asp Gly Val Glu Val
 65                  70                  75                  80

His Asn Ala Lys Thr Lys Pro Arg Glu Glu Gln Tyr Asn Ser Thr Tyr
                 85                  90                  95

Arg Val Val Ser Val Leu Thr Val Leu His Gln Asp Trp Leu Asn Gly
```

```
            100                 105                 110
Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
        130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
                180                 185                 190

Val Leu Asp Ser Asp Gly Ser Phe Phe Leu Tyr Ser Lys Leu Thr Val
                195                 200                 205

Asp Lys Ser Arg Trp Gln Gln Gly Asn Val Phe Ser Cys Ser Val Met
210                 215                 220

His Glu Ala Leu His Asn His Tyr Thr Gln Lys Ser Leu Ser Leu Ser
225                 230                 235                 240

Pro Gly Lys Gly Gly Gly Gly Ser Pro Pro Pro Met Ser Val Glu His
                245                 250                 255

Ala Asp Ile Trp Val Lys Ser Tyr Ser Leu Tyr Ser Arg Glu Arg Tyr
                260                 265                 270

Ile Cys Asn Ser Gly Phe Lys Arg Lys Ala Gly Thr Ser Ser Leu Thr
                275                 280                 285

Glu Cys Val Leu Asn Lys Ala Thr Asn Val Ala His Trp Thr Thr Pro
        290                 295                 300

Ser Leu Lys Cys Ile Arg Asp Pro Ala Leu Val His Gln Arg Pro Ala
305                 310                 315                 320

Pro Pro Ser Thr Val Ser Gly Gly Ser Gly Gly Ser Gly Ser Gly Gly
                325                 330                 335

Gly Ser Gly Gly Gly Ser Leu Gln Asn Trp Val Asn Val Ile Ser
                340                 345                 350

Asp Leu Lys Lys Ile Glu Asp Leu Ile Gln Ser Met His Ile Asp Ala
                355                 360                 365

Thr Leu Tyr Thr Glu Ser Asp Val His Pro Ser Cys Lys Val Thr Ala
        370                 375                 380

Met Lys Cys Phe Leu Leu Glu Leu Gln Val Ile Ser Leu Glu Ser Gly
385                 390                 395                 400

Asp Ala Ser Ile His Asp Thr Val Glu Asn Leu Ile Ile Leu Ala Asn
                405                 410                 415

Asn Ser Leu Ser Ser Asn Gly Asn Val Thr Glu Ser Gly Cys Lys Glu
                420                 425                 430

Cys Glu Glu Leu Glu Glu Lys Asn Ile Lys Glu Phe Leu Gln Ser Phe
        435                 440                 445

Val His Ile Val Gln Met Phe Ile Asn Thr Ser
        450                 455

<210> SEQ ID NO 6
<211> LENGTH: 1548
<212> TYPE: DNA
<213> ORGANISM: Artificial Sequence
<220> FEATURE:
<223> OTHER INFORMATION: Tumour-targeting fusion protein

<400> SEQUENCE: 6
aagcttctga gatcaccggc gaaggagggc caccatgtac aggatgcaac tcctgtcttg    60
```

```
cattgcacta agtcttgcac ttgtcacgaa ttcggcttgc gattgccgag gcgattgctt    120
ttgtggcctc gagggaggag gaggctccga caaaactcac acatgccac cgtgcccagc     180 acctgaactc ctgggggac cgtcagtctt cctcttcccc ccaaaaccca aggacaccct     240
catgatctcc cggacccctg aggtcacatg cgtggtggtg gacgtgagcc acgaagaccc     300
tgaggtcaag ttcaactggt acgtggacgg cgtggaggtg cataatgcca agacaaagcc     360
gcgggaggag cagtacaaca gcacgtaccg tgtggtcagc gtcctcaccg tcctgcacca     420
ggactggctg aatggcaagg agtacaagtg caaggtctcc aacaaagccc tcccagcccc     480
catcgagaaa accatctcca aagccaaagg cagccccga gaaccacagg tgtacaccct      540
gcccccatcc cggatgagc tgaccaagaa ccaggtcagc ctgacctgcc tggtcaaagg      600
cttctatccc agcgacatcg ccgtggagtg ggagagcaat gggcagccgg agaacaacta     660
caagaccacg cctcccgtgc tggactccga cggctccttc ttcctctaca gcaagctcac     720
cgtggacaag agcaggtggc agcaggggaa cgtcttctca tgctccgtga tgcatgaggc     780
tctgcacaac cactacacgc agaagagcct ccctgtctc cgggtaaag atatcggagg       840 aggaggctcc ccccctccta tgagcgtgga acatgctgac atttgggtga agtcttactc     900
tctgtacagt cgggagagat atatctgcaa ctcaggttc aagcgaaaag ccggaacaag      960
ctccctgact gaatgtgtgc tgaacaaggc cactaatgtc gctcactgga ccacacctag    1020
cctgaaatgc attagggacc cagcactggt gcatcagcga ccagcaccac cttcaaccgt    1080
cagcggaggg tccggaggag gaggatcagg aggggaagc ggcggaggag gcagcctgca     1140
gaactgggtg aatgtcatct ccgacctgaa gaaaatcgag gatctgattc agtccatgca    1200
cattgacgcc actctgtaca ccgaatccga tgtgcatccc tcttgcaagg tcacagctat    1260
gaaatgtttc ctgctggagc tgcaggtcat cagcctggaa agtggcgacg cttctattca    1320
cgataccgtg gagaatctga tcattctggc aaacaattct ctgtctagta acggcaatgt    1380
gacagagagt gggtgcaagg aatgtgagga actggaggaa aagaacatca agagttcct    1440 gcagagcttt gtgcatatcg tccagatgtt tattaatacc agctgagtgc gacggccggc    1500
aagcccccgc tccccgggct ctcgcggtcg cacgaggatg cttctaga                  1548
```

<210> SEQ ID NO 7
<211> LENGTH: 11
<212> TYPE: PRT
<213> ORGANISM: Artificial Sequence
<220> FEATURE:
<223> OTHER INFORMATION: RGD polypeptide as a component of the fusion
      protein for targeting integrin receptor expressed on tumor cell.

<400> SEQUENCE: 7

Ala Cys Asp Cys Arg Gly Asp Cys Phe Cys Gly
1               5                   10

<210> SEQ ID NO 8
<211> LENGTH: 4
<212> TYPE: PRT
<213> ORGANISM: Artificial Sequence
<220> FEATURE:
<223> OTHER INFORMATION: A RGD polypeptide variant as a component of the
      fusion protein for targeting integrin receptor expressed on tumor
      cell.

<400> SEQUENCE: 8

Gly Arg Gly Asp
1

```
<210> SEQ ID NO 9
<211> LENGTH: 7
<212> TYPE: PRT
<213> ORGANISM: Artificial Sequence
<220> FEATURE:
<223> OTHER INFORMATION: A RGD polypeptide variant as a component of the
      fusion protein for targeting integrin receiptor expressed on tumor
      cell.

<400> SEQUENCE: 9

Gly Arg Gly Asp Ser Pro Cys
1               5

<210> SEQ ID NO 10
<211> LENGTH: 7
<212> TYPE: PRT
<213> ORGANISM: Artificial Sequence
<220> FEATURE:
<223> OTHER INFORMATION: A RGD polypeptide variant as a component of the
      fusion protein for targeting integrin receiptor expressed on tumor
      cell.

<400> SEQUENCE: 10

Gly Arg Gly Asp Asp Ser Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: A RGD polypeptide variant as a component of the
      fusion protein for targeting integrin receiptor expressed on tumor
      cell.

<400> SEQUENCE: 11

Glu Pro Arg Gly Asp Asn Tyr Arg
1               5

<210> SEQ ID NO 12
<211> LENGTH: 5
<212> TYPE: PRT
<213> ORGANISM: Artificial Sequence
<220> FEATURE:
<223> OTHER INFORMATION: A linker for linking between components of the
      fusion protein.

<400> SEQUENCE: 12

Gly Gly Gly Gly Ser
1               5

<210> SEQ ID NO 13
<211> LENGTH: 20
<212> TYPE: PRT
<213> ORGANISM: Artificial Sequence
<220> FEATURE:
<223> OTHER INFORMATION: A linker for linking between components of the
      fusion protein.

<400> SEQUENCE: 13

Ser Gly Gly Ser Gly Gly Gly Gly Ser Gly Gly Gly Ser Gly Gly Gly
1               5                   10                  15

Gly Ser Leu Gln
            20
```

INTERLEUKIN 15 FUSION PROTEIN FOR TUMOR TARGETING THERAPY

CROSS REFERENCE TO RELATED APPLICATIONS

This application is a continuation application of U.S. patent application Ser. No. 15/747,029, filed Jan. 23, 2018, now U.S. Pat. No. 10,611,812, which is a national stage of PCT/CN2016/088158, filed Jul. 1, 2016, which claims priority from Chinese patent application number 201510378781.2, filed Jul. 2, 2015, the content of each of which are hereby incorporated by reference in their entireties.

FIELD OF THE INVENTION

The present invention relates to the use of interleukin-15 in tumor targeting therapy, and in particular, to the anti-tumor activity of an interleukin-15 fusion protein.

BACKGROUND

Cytokines play important roles in the regulation of the immune system, including anti-tumor immune responses. A number of cytokines have been shown to have anti-tumor potential. Among these cytokines, interleukin-15 (IL-15) has been extensively studied as a promising anti-tumor candidate. IL-15 belongs to the common receptor γ-chain cytokine family that also includes IL-2. IL-15 and IL-12 share the β- and γ-chains of their receptors (IL-2/15βγ), but bind to different α receptor chains (IL-2Rα/IL-15Rα). IL-15 binds to IL-15Rα expressed on antigen presenting cells and the IL-15/IL-15Rα complex then binds to the IL-15βγ complex expressed on nearby effector cells. Similar to IL-12, IL-15 can stimulate the proliferation of T cells and natural killer (NK) cells, the expansion of cytotoxic T cells and the activation of NK cells. Unlike IL-12, IL-15 is not involved in the activation-induced cell death and maintenance of regulatory T cells, which can block the therapeutic effects of IL-2. Thus, IL-15 is ranked at the top of the National Cancer Institute's list of agents with great potential for cancer immunotherapy.

However, recent studies have suggested that in vivo anti-tumor effects of IL-15 could only be achieved at high dosage. Another limitation of IL-15 as a therapeutic agent is its short plasma half-life. One potential limitation of these efforts is that the function of IL-15 is systemic and not tumor specific. In response to a long IL-15 half-life, cytotoxic T cells or NK cells are expanded systemically, not only in tumors. As uncontrolled systemic activation of the immune system can be very toxic and lethal, a more desirable therapeutic agent will need to be able to limit its function to tumors and spare other tissues to reduce toxicity. Therefore, an ideal candidate should be tumor-targeting without substantial affects to normal tissues.

SUMMARY

The present invention provides a tumor-targeting fusion protein which, in one aspect, has improved IL-15 anti-tumor activity, and in another aspect, overcomes the problems associated with short half-life of IL-15. The fusion protein can target tumor site and act on tumor cells only.

The fusion protein provided by the invention comprises at least (i) a IL-15 polypeptide or a variant or a functional fragment thereof, (ii) a IL-15Rα polypeptide or a variant or a functional fragment thereof, (iii) a Fc domain or a variant or a functional fragment thereof, and (iv) a RGD polypeptide or a variant thereof.

In one embodiment, the fusion protein has components arranged as RGD-Fc-IL-15-IL-15Rα.

In one embodiment, the Fc domain is comprised of CH2 and CH3 of human IgG1 and has an amino acid sequence SEQ ID NO:1 or an equivalent thereof that has substitution, deletion or addition of one or more amino acids but retains the function of the Fc domain.

In one embodiment, the IL-15Rα is comprised of a IL-15Rα sushi domain including the subsequent 12 amino acids from exon 3 and has an amino acid sequence SEQ ID NO:2 or an equivalent thereof that has substitution, deletion or addition of one or more amino acids but retains the function of the IL-15Rα domain.

In one embodiment, the IL-15 has an amino acid sequence SEQ ID NO:3 or an equivalent thereof that has substitution, deletion or addition of one or more amino acids but retains the function of the IL-15 domain.

In one embodiment, the RGD polypeptide has an amino acid sequence SEQ ID NO:4 or an equivalent thereof that has substitution, deletion or addition of one or more amino acids but retains the function of the RGD polypeptide.

In a preferable embodiment, the tumor-targeting fusion protein has an amino acid sequence selected from a group consisting of: (a) an amino acid sequence of SEQ ID NO: 5; (b) an amino acid sequence encoded by a nucleic acid sequence of SEQ ID NO:6; (c) an amino acid sequence encoded by a degenerate sequence of the nucleic acid sequence of SEQ ID NO:6; and (d) an equivalent amino acid sequence of SEQ ID NO: 5 that has substitution, deletion or addition of one or more amino acids but retains the function of the fusion protein.

In another aspect, the present invention provides a pharmaceutical composition comprising a tumor-targeting fusion protein of the present invention and a pharmaceutically acceptable excipient including a carrier, a stabilizing agent and/or a vehicle. In one embodiment, the present invention provides a pharmaceutical composition comprising a tumor-targeting fusion protein of the present invention and a further anti-tumor agent.

In one embodiment, the tumor is an integrin positive tumor, and in particular, a αVβ3 integrin positive tumor including melanoma or ovarian cancer. In one embodiment, the tumor is a progressive tumor, an advanced tumor, a tumor with a high burden/load, or a metastatic tumor.

In another aspect, the present invention provides a nucleic acid sequence encoding the tumor-targeting fusion protein, an expression vector comprising the nucleic acid sequence, or a host transformed or transfected by the expression vector.

In another aspect, the present invention further provides a kit comprising a tumor-targeting fusion protein of the present invention, a nucleic acid sequence encoding the tumor-targeting fusion protein, an expression vector comprising the nucleic acid sequence, or a host transformed or transfected by the expression vector.

The tumor-targeting fusion proteins provided by the invention improves the anti-tumor effects of IL-15 and prolongs the half-life of IL-15, while targeting tumor sites and acting upon tumor cells. In addition, the fusion proteins are capable of being expressed at high efficiency and purified. The high efficiency of anti-tumor activity enables the fusion proteins to be an excellent candidate for tumor immunotherapy.

DETAILED DESCRIPTION OF THE INVENTION

Fusion Proteins

As used exchangeable herein, the terms "fusion protein", "PFC-1", "PFC-1 recombinant fusion protein" and "fusion molecule" refer to a biologically active polypeptide formed by more than one protein or peptide sequences covalently linked (i.e., fused) by recombinant, chemical or other proper methods. A fusion protein can be fused to other peptide or protein sequence at one or more site through a linker sequence. Alternatively, a linker sequence can be used to assist construction of a fusion molecule. A fusion protein may exist in the form of a monomer or a multimer, e.g., a dimer.

In the present invention, a "fusion protein" comprises at least (i) a IL-15 polypeptide or a variant or functional fragment thereof, (ii) a IL-15Rα polypeptide or a variant or functional fragment thereof, (iii) a Fc domain or a variant or functional fragment thereof, and (iv) a RGD polypeptide or a variant thereof. In the fusion protein, components (i) and (ii) jointly constitute an effector module or molecule which can induce the activation of effector cells (cytotoxic T cells and NK cells). Component (iii) is included to prolong the circulating half-life of IL-15. Component (iv) is a targeting molecule which acts with high affinity and specificity on the receptor molecules expressed on the surfaces of tumor cells, such that the remaining components are enriched within the tumor site and kill the tumor cells.

In the invention described herein, the components of the fusion protein are properly arranged such that the fusion protein achieves the expected purpose of the invention. In one embodiment, the components of the fusion protein are arranged as RGD polypeptide-Fc domain-IL15 polypeptide-IL15Rα polypeptide. In another embodiment, the components of the fusion protein are arranged as RGD polypeptide-Fc domain-IL15Rα polypeptide-IL15 polypeptide. In another embodiment, the components of the fusion protein are arranged as RGD polypeptide-IL15Rα polypeptide-IL15 polypeptide-Fc domain. In another embodiment, the components of the fusion protein are arranged as RGD polypeptide-IL15 polypeptide-IL15Rα polypeptide-Fc domain. A person skilled in the art can obtain the fusion proteins as described above by gene engineering or relevant technologies and verify the biological functions thereof without requiring creative work.

Fc Domain

The term "Fc domain" or "Fc fragment" refers to the "crystallizable fragment" region of a heavy chain of an immunoglobin. Generally, a Fc domain can interact with another Fc domain to form a dimer complex. Fc domain binds to a cell surface receptor (Fc receptor) and/or proteins of complement system, or it can be modified to reduce or enhance such binding. Fc domain is derivable from IgG, IgA, IgD, IgM or IgE and has immunological functions including Fc receptor dependent procedures such as opsonization, cell lysis, and mast cells degranulation.

IgG type immunoglobins are among the most abundant proteins in human blood and have a circulating half-life as long as 21 days. Fusion proteins have been reported to combine the Fc regions of IgG with the domains of another protein. The prototype fusion protein is a homodimeric protein liked through cysteine residues in the hinge region of IgG Fc, resulting in a molecule similar to an IgG molecule without the heavy chain variable and CH1 domains and light chains. The dimer nature of fusion proteins comprising the Fc domain may be advantageous in providing higher order interactions (e.g. bivalent or bispecific binding) with other molecules. Due to the structural homology, Fc fusion proteins exhibit in vivo pharmacokinetic profile comparable to that of human IgG with a similar isotype. To extend the circulating half-life of the IL-15 cytokine, it is desirable to link the IL-15/IL-15Rα complex to the Fc portion of the human heavy chain IgG protein. The original immunoglobin source of the native Fc is preferably of human origin and may be any of the immunoglobins, although IgG1 and IgG2 are preferred.

In some embodiments, the term "Fc variant" refers to a molecule or sequence that is modified from a native Fc but still comprise a binding site for the salvage receptor, FcRn. "Fc domain" comprises a molecule or sequence that is humanized from a non-human native Fc. Furthermore, a native Fc comprises sites that may be removed because they provide structural features or biological activity that are not required for the fusion proteins of the present invention. Thus, in certain embodiments, the term "Fc variant" comprises a molecule or sequence that lacks one or more native Fc sites or residues. The term "Fc domain" encompasses native Fc and Fc variant molecules and sequences as defined above, including molecules in monomeric or multimeric form, whether digested from whole antibody or produced by recombinant gene expression or by other means.

RGD Polypeptides

Arg-Gly-Asp (RGD) was found by Pierschbacher and Rouslahti in 1984 in FN as a cell adhesion sequence. They found RGD polypeptide was able to elute integrin α5β1 from affinity column and to adhere to cells when immobilized on a matrix material. Then, many glycoproteins (such as LM), collagen, fibrinogen (Fb) in the extracellular matrix were found to have highly conservative RGD polypeptide, and it was demonstrated to play an important role in the mediation of the interactions among cell-cell and cell-extracellular matrix proteins.

The binding of RGD polypeptide to a cell is a binding to the integrins on the cell surface. Integrin was found in 1990s and belongs to $Ca^{2+}$ dependent cell surface receptor family. Each integrin comprises 2 subunits: α subunit and β subunit. 18 α subunits and 8 β subunits have been found so far, constituting 24 types of integrins. Integrin that can recognize RGD polypeptide and bind thereto include α3β1, α5β1, αIIbβ3, α5β1, αvβ1, αvβ3, αvβ5, αvβ6, αvβ8 and so on. RGD polypeptide shows extremely strong affinity and selectivity to αvβ3 integrin. αvβ3 integrin was highly overexpressed in various tumor cells and endothelial cells generated by tumor related angiogenesis.

In the invention described herein, the drug was conjugated or fused with RGD polypeptide which directs the selective enrichment of the fusion molecule to the tumor tissue, resulting in increased local drug concentration and enhanced tumor killing effects, while limiting systemic toxicity.

RGD tripeptide is biological inactive and the fourth amino acid adjoining the RGD tripeptide substantially affects its activity. The fifth amino acid adjoining the RGD tripeptide plays an important role in the binding specificity. It was demonstrated that addition of residues at the N terminal of the RGD tripeptide did not interrupt its adherence to cells. For example, RGD tripeptide and GRGD tetrapeptide do not exhibit significant difference in cell adherence. On the contrary, amino acid addition at the C terminal would alter its cell adherence. For instance, addition of Serine following the Asp residue would enhance the cell adherence activity, while a right-handed residue in replace of a left-handed residue would damage the cell adherence.

In one embodiment of the present invention, the RGD polypeptide has an amino acid sequence ACDCRGDCFCG, i.e., Ala Cys Asp Cys Arg Gly Asp Cys Phe Cys Gly, in which the RGD motif is located at the $5^{th}$ to $7^{th}$ amino acids.

In the invention, the term "RGD variant" refers to a polypeptide having at least one amino acid substitution, deletion or insertion compared to the RGD polypeptide sequence but still maintaining the integrin receptor binding function. A person skilled in the art could design one or more RGD polypeptide variant based on the disclosure of the present invention and known techniques. Exemplary RGD variants include GRGD, GRGDSPC, GRGDDSY, EPRGDNYR and so on.

Linkers

The fusion proteins of the invention may also include a linker between components. The linker is normally a short polypeptide comprised of 4 to 20 amino acids. The linkers allow effective positioning of each components to allow functional activity of these domains.

In certain embodiments, in the fusion proteins of the present invention, IL-15 polypeptide is covalently liked to IL-15Rα polypeptide so that IL-15 and IL-15Rα domains are capable of interacting with each other to form a protein complex. In certain embodiments, the IL-15 and IL-15Rα domains are effectively positioned to allow interactions with immune cells to initiate or inhibit an immune reaction, or to inhibit or stimulate cell development.

In some embodiments, in the fusion proteins of the invention, IL-15 or IL-15Rα domain is covalently linked to the Fc domains through a linker. The liker sequence should allow effective positioning of the Fc, IL-15 or IL-15Rα domains to allow functional activity of each domain. In certain embodiments, the Fc domains are effectively positioned to allow proper fusion protein complex formation and enhanced in vivo half-life of the fusion protein complex.

In some embodiments, in the fusion proteins of the invention, RGD polypeptide is covalently linked to the Fc domains through a linker. The liker sequence should allow effective positioning of the RGD and Fc domains to allow functional activity of each domain. In certain embodiments, the RGD domains are effectively positioned to allow binding to integrin on tumor cell surface at a high affinity and specificity.

Preferably, the linker sequence comprises from about 2 to 20 amino acids, more preferably from about 5 to 20 amino acids. The linker sequence is preferably flexible so as not hold the effector molecule in a single undesired conformation. The linker sequence can be used, e.g., to space the recognition site from the fused molecule. The linker preferably predominantly comprises amino acids with small side chains, such as glycine, alanine and serine, to provide for flexibility. Preferably about 80 or 90 percent or greater of the linker sequence comprises glycine, alanine and serine, particularly glycine and serine residues. Examples of suitable linker sequence are GGGGS ($G_4S$), i.e. Gly Gly Gly Gly Ser, which is used for example to link the RGD polypeptide to the Fc domain, and the Fc domain to the IL-15Rα polypeptide; and $SG_2SG_4SG_3SG_4SLQ$, i.e. Ser Gly Gly Ser Gly Gly Gly Gly Ser Gly Gly Gly Ser Gly Gly Gly Gly Ser Leu Gln, which is used for example to link the IL-15 to IL-15Rα domains. Different linker sequences could be used including any of a number of flexible linker designs that have been used successfully to join antibody variable regions together. Additionally, suitable size and sequences of linker sequences also can be determined by conventional computer modeling techniques.

The term "polypeptide' is meant to refer to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide variant" refers to an amino acid sequence has one or more amino acid substitution, deletion or insertion compared to the polypeptide sequence but still maintaining the biological function of the polypeptide.

The term "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

Materials and Methods

Antibodies: Recombinant human IL-2 (AF-200-02) and granulocyte-macrophage colony-stimulating factor (300-03) were purchased from Peprotech. Recombinant human IL-15 (247-IL-105) was purchased from R&D Systems. Anti-MsCD3e (145-2c11)-PerCP, anti-MsCD8a(53-6.7)-FITC, anti-MsNK1.1(PK136)-FITC, anti-MsCD44(IM7)-PE and anti-MsCD122(TM-Bta1)-PE were purchased from BD PharMingen. Anti-human CD51/61 (αvβ3 integrin) purified mAb was purchased from eBioscience. Goat anti-human IgG($H^+L$)-AlexaFluor 488, goat anti-mouse IgG($H^+L$)-AlexaFluor 488 and goat anti-Mouse IgG($H^+L$)-AlexaFluor 647 were purchased from Invitrogen.

Cell lines and animals: SKOV-3, CTLL-2, and Mo7e cells were purchased from the Shanghai Cell Bank. HUVEC cells were kindly gifted by Dr. Gao Huile from Sichuan University. CTLL-2 cells were cultured in RPMI 1640 supplemented with 20% fetal bovine serum (FBS), 30 ng/ml IL-2, and 1% non-essential amino acids. Mo7e cells were cultured in RPMI 1640 supplemented with 10% fetal bovine serum (FBS), 10 ng/ml GM-CSF, and 1% non-essential amino acids. SKOV-3 and HUVEC cells were cultured in DMEM supplemented with 10% FBS. PBMC were isolated from the buffy coat of healthy donors using Ficoll-Paque plus (GE health) and cultured in RPMI-1640 supplemented with 10% FBS. C57bl/6 mice were purchased from the Animal Experiment Facility of Sun Yat-sen University. Human blood collection, animal care and animal experiments were approved by Sun Yat-sen University.

Expression and Purification of the Fusion Protein

Generally, the fusion proteins of the invention could be prepared by the procedures disclosed herein or other DNA recombinant techniques in the art, for example, PCR, plasmid DNA extraction, DNA digestion by restriction endonucleases, DNA ligation, mRNA isolation, introduction of DNA into suitable cells, transformation and transfection of host cells, culture of host cells and so on. Additionally, the fusion proteins can be isolated and purified by suitable agents and known methods, including electrophoresis, centrifugation, chromatography and etc.

To generate the recombinant protein PFC-1, the fusion gene (PFC-1) was cloned into the pcDNA3.1 (+) vector with a mouse kappa chain signal peptide. The plasmid was transiently transfected to 293 cells. One hundred ml of media were collected after 3 d of culture. The PFC-1 protein was purified with a Protein-A-agarose affinity purification protocol.

Figure 1:
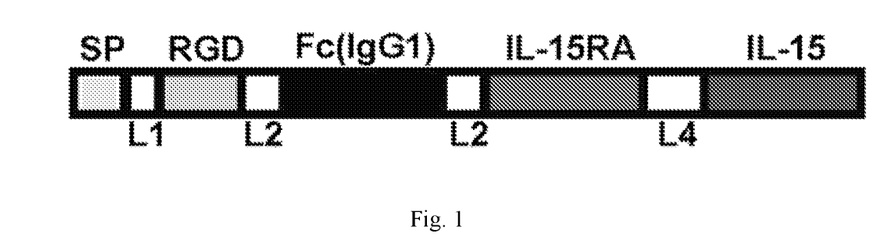
FIG. 1 is a schematic view of a tumor-targeting fusion protein according to one embodiment (PFC-1). SP, signal peptide; RGD, Arginine-Glycine-Aspartate peptide motif; Fc, CH2 and CH3 of human IgG1; IL-15Ra, IL-15Rα sushi domain+the subsequent 12 amino acids from exon 3; L1, SS; L2, G₄S; L4, SG₂SG₄SG₃SG₄SLQ.

The fusion protein PFC-1 is shown in FIG. 1, which comprises the following 3 parts: (1) IL-15/IL15Rα complex, (2) an Fc domain, and (3) a RGD peptide. The parts are linked by a linker GGGGS, and a His-tag is attached to the C terminal of the fusion protein (FIG. 1). The DNA sequence was cloned into the pCDNA3.1(+) vector and then transiently transfected into HEK293 cells to express.

Figure 2:
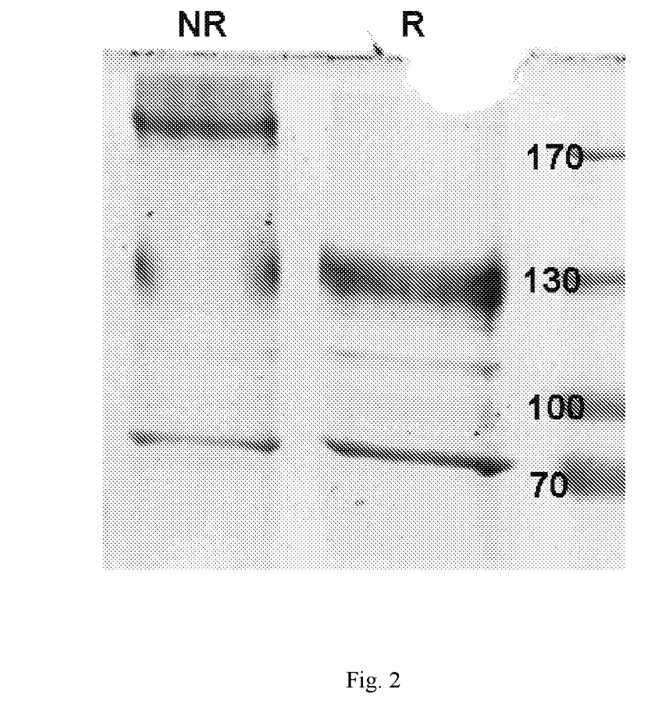
FIG. 2 is Coomassie blue staining of the fusion protein developed from 10% SDS-PAGE under non-reducing (NR) or reducing (R) conditions.

A single band of approximately 60 kDa was observed under reducing conditions (FIG. 2). Under non-reducing conditions, the majority of the protein is approximately 120 kDa with a minor product at approximately 60 kDa. The results suggested that a homogenous PFC-1 fusion protein was obtained by mammalian expression and affinity purification, and the majority of the PFC-1 protein was in a dimeric form.

Cytokine-Dependent Cell Proliferation Assay

To measure cytokine-dependent cell proliferation, CTLL-2 and Mo7e cells were harvested in their logarithmic growth phase, washed twice with PBS and incubated for 4 h in assay medium (RPMI 1640 supplemented with 10% FBS and 1% NEAA) for cytokine starvation at 37° C. and 5% CO2. During the incubation, IL-15 and PFC-1 were diluted to an initial concentration of 10 nM in the assay medium, followed by serial dilutions. After a 4-h incubation, cells were collected and a cell suspension ($2 \times 10^4$ cells/well) was seeded immediately into corresponding wells and incubated at 37° C. and 5% CO2 for 48 or 72 h with CTLL-2 or Mo7e cells, respectively. After a 48-h or 72-h incubation period, CCK-8 assay (Dojindo) was performed to measure the amount of live cells.

CTLL-2 is a murine cytotoxic T lymphocytic cell line with positive expression of both the IL-15Rα chain and the IL-15βγ complex, while Mo7e is a human megakaryocytic leukemic cell line that only expresses the IL-15βγ complex. Proliferation of both cell lines can be induced by the presence of IL-15. Similar to IL-15, PFC-1 can stimulate the proliferation of both Mo7e and CTLL-2 cell lines (FIGS. 3 and 4), demonstrating the IL-15 cytokine activity of PFC-1

Figure 3:
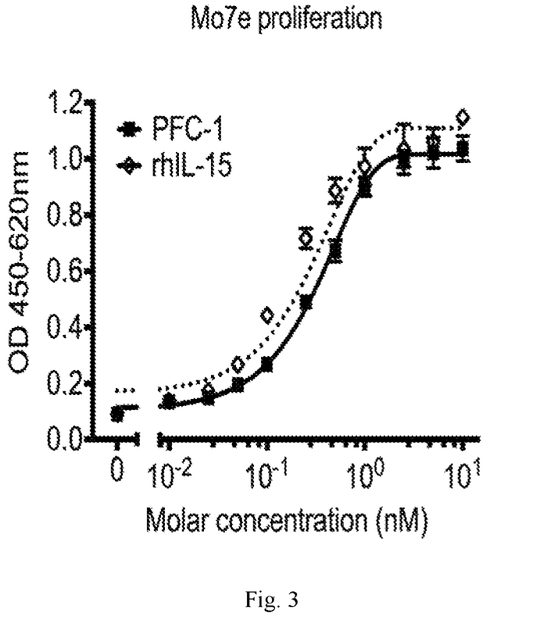
FIG. 3 shows Mo7e proliferation stimulated by rhIL-15 and PFC-1. The concentration was calculated according to the molecular weight of a PFC-1 monomer. The data are shown as the mean±SD of triplicate samples. The results are representative of at least 3 experiments.
Figure 4:
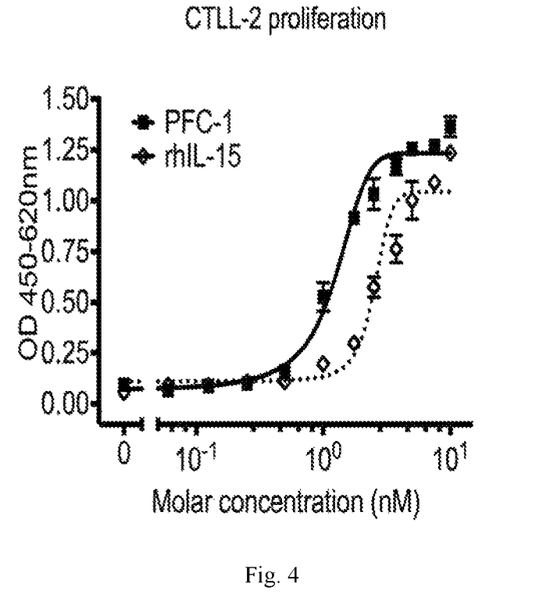
FIG. 4 shows CTLL-2 proliferation stimulated by rhIL-15 and PFC-1. The concentration was calculated according to the molecular weight of a PFC-1 monomer. The data are shown as the mean±SD of triplicate samples. The results are representative of at least 3 experiments.

When the molar concentration of PFC-1 was calculated as a monomer in Mo7e cells, rhIL-15 showed a slightly higher cytokine activity than PFC-1 (FIG. 3). However, no difference was observed at 10 nM. PFC-1 worked better than rhIL-15 in CTLL-2 cells, with approximately 2- to 4-fold stronger activity (FIG. 4).

CFSE Labeling of PBMC and Proliferation Assay

To measure PBMC proliferation, PBMCs were freshly prepared by Ficoll centrifugation, adjusted to $2\times10^6$ cells/ml, and then stained with 5 µM CFSE (eBioscience) according to the manufacturer's instructions. Stained PBMCs ($5\times10^5$ cell/ml) were incubated with 1 nM or 10 nM of rhIL-15 and PFC-1 for 6 d PBMC proliferation was assessed by flow cytometry using a Cytomic FC500 (Beckman Coulter) and analyzed using the Kaluza software (Beckman Coulter).

Figure 5:
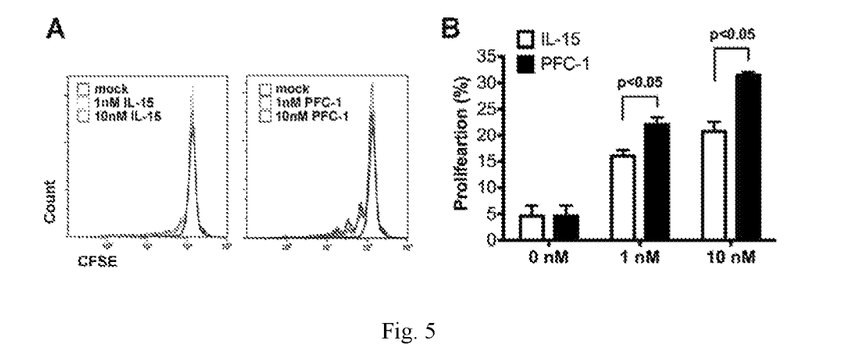
FIG. 5 shows the PBMC proliferation stimulation in vitro by PFC-1. CFSE-labeled PBMCs were incubated with various concentrations of rhIL-15 or PFC-1 for 6 d. Proliferation of PBMCs was assessed by flow cytometry. (A) Representative FACS images of PBMC proliferation are shown. (B) Quantitative analysis of PBMC proliferation stimulation by rhIL-15 or PFC-1. The concentration was calculated according to the molecular weight of a PFC-1 monomer. The data are shown as the mean±standard deviation of triplicate samples. The results are representative of 3 experiments.

To measure the activity of PFC-1 on primary immune cells, PBMCs (Peripheral blood mononuclear cells) were prepared, stained with CFSE and incubated with rhIL-15 or PFC-1 for 6 d. Both rhIL-15 and PFC-1, at either 1 or 10 nM, significantly stimulated the proliferation of PBMCs compared to the control group (FIG. 5). However, different from the Mo7e and CTLL-2 cytokine-dependent proliferation assay, PFC-1 exhibited an approximately 10-fold stronger potency than rhIL-15 in PBMC proliferation, while 10 nM rhIL-15 led to a proliferation rate of 20.71% and 1 nM PFC-1 resulted in a mean value of 22.05% (FIG. 5). The enhanced activity could be due to the higher activity of IL-15/IL-15Rα than IL-15, the extended half-life by the Fc fragment, or both.

Colocalization of PFC-1 and Integrin

Figure 6:
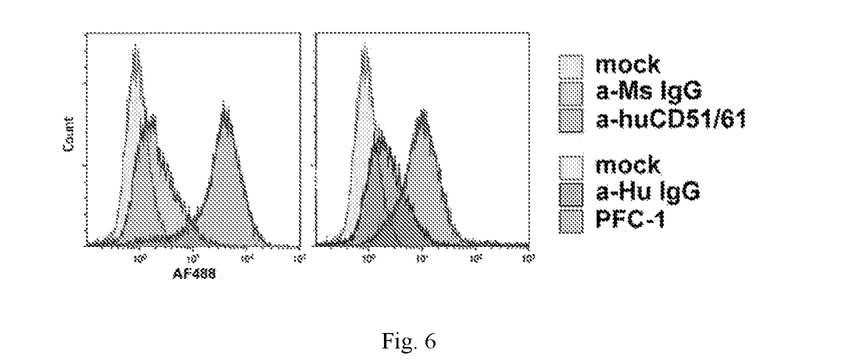
FIG. 6 shows the binding of the fusion protein PFC-1 to HUVEC cell lines by flow cytometry. Results represented at least three independent experiments.
Figure 7:
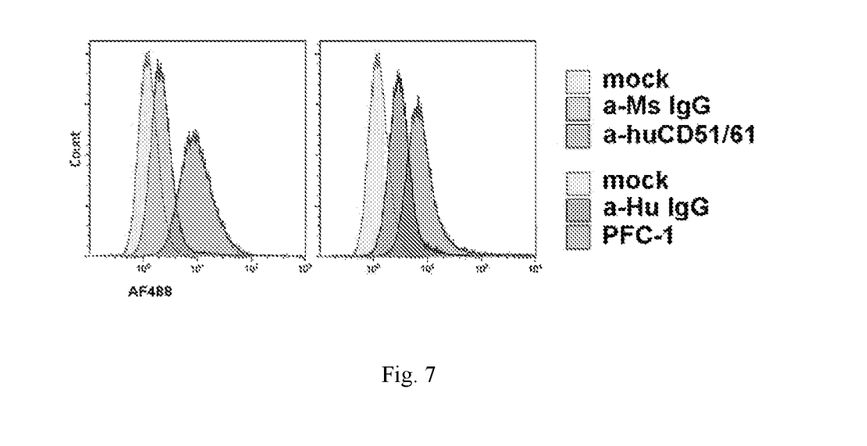
FIG. 7 shows the binding of the fusion protein PFC-1 to SKOV-3 tumor cell lines by flow cytometry. Results represented at least three independent experiments.
Figure 8:
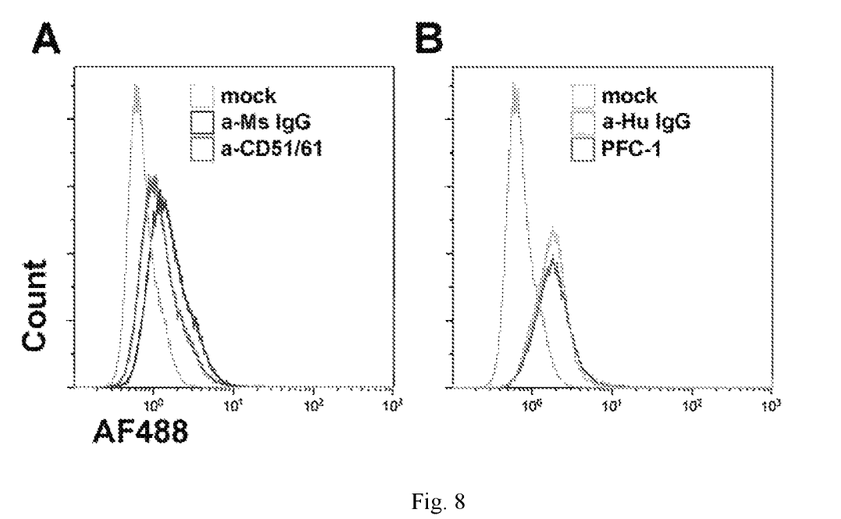
FIG. 8 shows the binding of the fusion protein PFC-1 to LS74T tumor cell lines by flow cytometry. Results represented at least three independent experiments.

To confirm that PFC-1 can indeed bind to tumor cells or tumor endothelial cells through cell surface integrins, HUVEC endothelial cells or SKOV3 ovarian cancer cells were used to check PFC-1 binding as both of these cell lines have high expression of $\alpha v\beta_3$ integrins. Flow cytometry analysis suggested that both HUVEC (FIG. 6) and SKOV3 cells (FIG. 7) are indeed $\alpha v\beta_3$-integrin positive. The colon cancer cell line LS174T is $\alpha v\beta_3$-integrin negative (FIG. 8). Therefore, these three cell lines were used to verify the colocalization of the PFC-1 and integrin.

Cells were trypsinized, adjusted to $4\times10^5$ cells/ml and incubated in complete DMEM medium for 2 hr at 37° C. Cells were then washed with PBS and aliquoted to a concentration of $2\times10^5$ cell/500 µl. Then, the cells were stained with 2 µg of anti-human CD51/61 ($\alpha v\beta_3$ integrin) or PFC-1, followed by incubation with a fluorophore-conjugated secondary antibody before being subjected to flow cytometry analysis.

When coincubated with HUVEC or SKOV3 cells, PFC-1 can bind to HUVEC (FIG. 6) and SKOV3 (FIG. 7) cells, though weaker than the anti-$\alpha v\beta_3$ integrin mAb. However, no binding was observed for the colon cancer cell line LS174T, regardless of PFC-1 or the anti-$\alpha v\beta_3$ integrin mAb (FIG. 8). Flow cytometry shows that PFC-1 could specifically bind to the HUVEC or SKOV3 cell surfaces.

Confocal Microscopy

SKOV3 and HUVEC cells were cultured on 30-mm glass-bottom dishes (In Vitro Scientific) to 70% confluence. The cells were then washed with cold PBS and fixed with 4% paraformaldehyde. The fixed cells were incubated with 2 µg of purified anti-human CD51/61 ($\alpha v\beta_3$ integrin) or PFC-1 at room temperature for 1 hr, followed a second incubation at room temperature for 1 hour with either goat anti-mouse IgG-AlexaFluor 647 or goat anti-human IgG-AlexaFluor 488, respectively. The nuclei were counterstained with DAPI. Zeiss LSM710 confocal microscopy was used to observe the cells.

Figure 9:
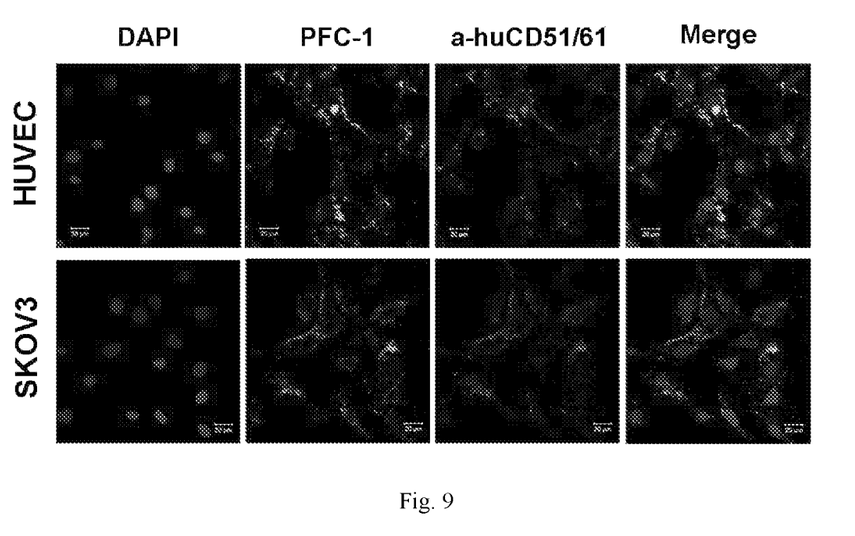
FIG. 9 shows the colocalization of the fusion protein PFC-1 with anti-human CD51/61 (αVβ3 integrin) antibody on HUVEC cell and SKOV3 tumor cell models by laser confocal microscopy.

Imaging analysis showed that PFC-1 co-localized with the anti-$\alpha v\beta_3$ integrin mAb on both HUVEC and SKOV3 cells (FIG. 9), indicating PFC-1 and the anti-αVβ3 integrin mAb bind to the same cell surface protein (i.e., αVβ3-integrin in this case), although via different protein epitopes.

The results of flow cytometry and confocal microscopy suggested that PFC-1 specifically binded to $\alpha v\beta_3$-integrin via RGD motif and therefore achieved specific targeting to $\alpha v\beta_3$-integrin expressing tumor cells in vitro.

PFC-1 has High In Vivo Anti-Tumor Efficacy

Figure 10:
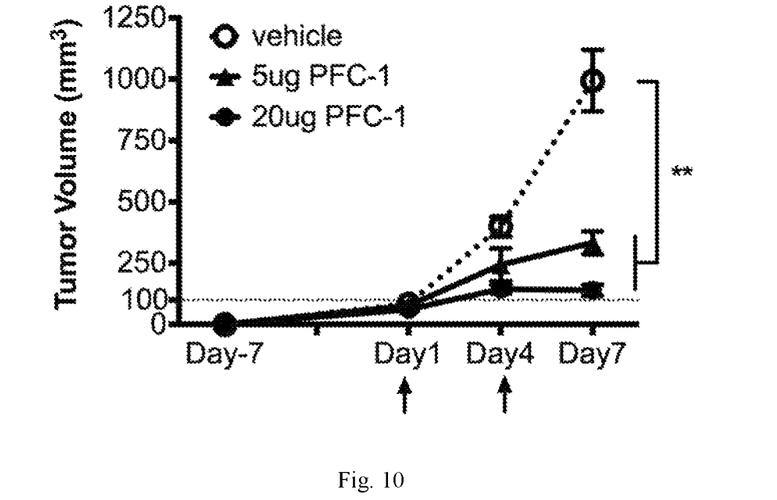
FIG. 10 shows the in vivo anti-tumor activity of the fusion protein in mouse. The mice were subcutaneously inoculated with B16F10 mouse melanoma cells on the back. When the size of the tumor reached 100 mm³ in volume, the mice were intraperitoneally injected with 5 or 20 μg PFC-1, or 200 μl PBS every 3 days. The mice received two injections and the tumor size was measured. Results represented at least three independent experiments (n=5-8 for each group). T-test was used for statistical analysis, ** represents $p<0.01$.

For the anti-tumor studies, 4-6-week old female C57bl/6 mice were injected with $5\times10^5$ B16F10 mouse melanoma tumor cells at the right flank. Ten to 12 d later, once tumors reached 5-8 mm in diameter (day 0). When the tumors reached 50-100 mm$^3$, the mice were administered with different dosages of PFC-1 or negative control (PBS). The tumor size was measured at scheduled dates. Results showed that 5 µg PFC-1 treatment was able to restrain tumor growth by 70%, while the 20 µg PFC-1 treatment was able to completely (100%) abrogate tumor growth (FIG. 10).

Figure 11:
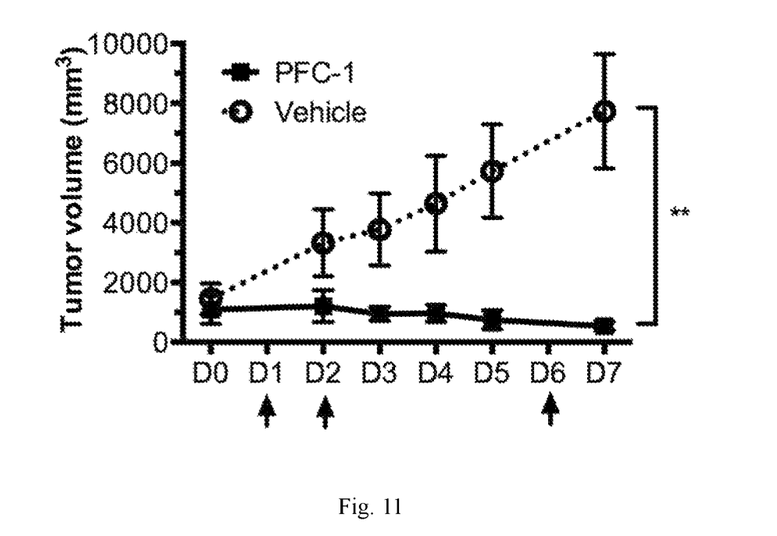
FIG. 11 shows the in vivo anti-tumor activity of the fusion protein in mouse. The mice were subcutaneously inoculated with B16F10 mouse melanoma cells on the back. When the size of the tumor reached 1000 mm³ in volume, the mice were injected via tail vein with 10 μg PFC-1, or 200 μl PBS on scheduled dates. The mice received three injections and the tumor size was measured every day. Results represented at least three independent experiments (n=5-8 for each group). T-test was used for statistical analysis, ** represents $p<0.01$.

In a similar experiment in mouse model, 4-6-week old female C57BL/6 mice were inoculated intravenously with $5\times10^5$ B16F10 cells. After large tumor burdens were established, 10 µg PFC-1 was injected intravenously for 2 consecutive days. Potent in vivo tumor growth blockage was observed (FIG. 11). On day 5, the tumor volume had shrunk by 25% after PFC-1 treatment (FIG. 11) compared to the initial tumor volume. With an additional PFC-1 treatment on day 6, tumor volumes decreased to 54% of the initial tumor volume.

Phenotypic Characterization by Flow Cytometry

Peripheral blood was collected from the orbital vein. Spleens were removed and splenocytes were processed into single cell suspensions and filtered through a 70-µm nylon mesh (BD). Tumor tissues were also removed and gently disrupted with forceps followed by enzymatic digestion with 0.2 mg/ml collagenase IV (Sigma) and 0.1 mg/ml DNase I (Sigma) in RPMI-1640 at 37° C. for 15 min. The released cells were collected and the remaining tumor tissue was subjected to further processing by incubation in fresh digestion medium for an additional 25 min at 37° C. Single-cell suspensions were filtered with a 70-um nylon mesh. Cell samples from the blood, spleen and tumor tissues were then stained with the corresponding antibodies at room temperature for 30 min, protected from light. Samples were then washed with PBS twice and adjusted to an appropriate volume for flow cytometry analysis.

Figure 12:
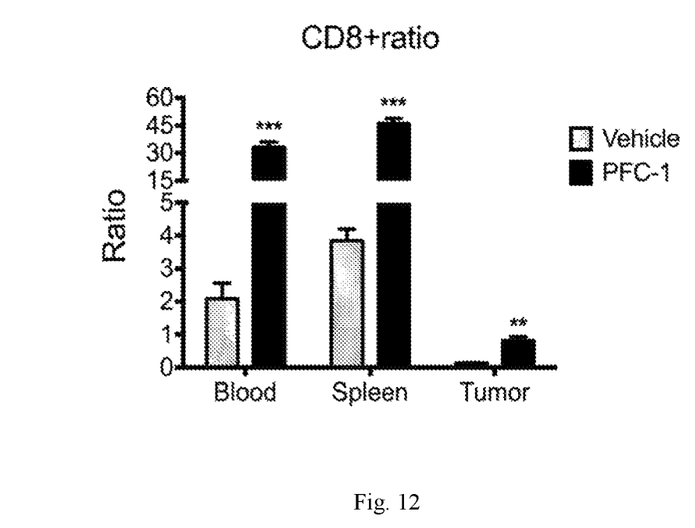
FIG. 12 shows the phenotype change of CD8+ T cells of the mice received PFC-1 treatment in FIG. 10 by flow cytometry. Results represented at least three independent experiments (n=5-8 for each group). T-test was used for statistical analysis,  represents $p<0.01$, * represents $p<0.005$.
Figure 13:
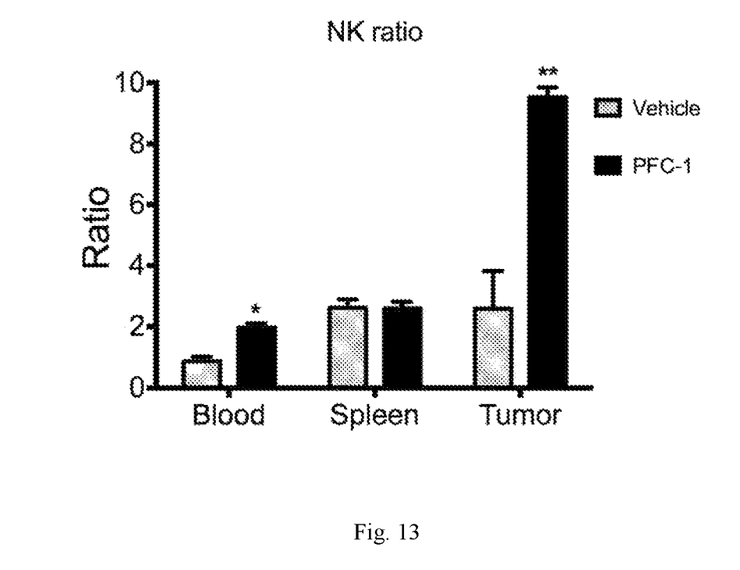
FIG. 13 shows the phenotype change of NK cells of the mice received PFC-1 treatment in FIG. 10 by flow cytometry. Results represented at least three independent experiments (n=5-8 for each group). T-test was used for statistical analysis,  represents $p<0.01$, * represents $p<0.005$.
Figure 14:
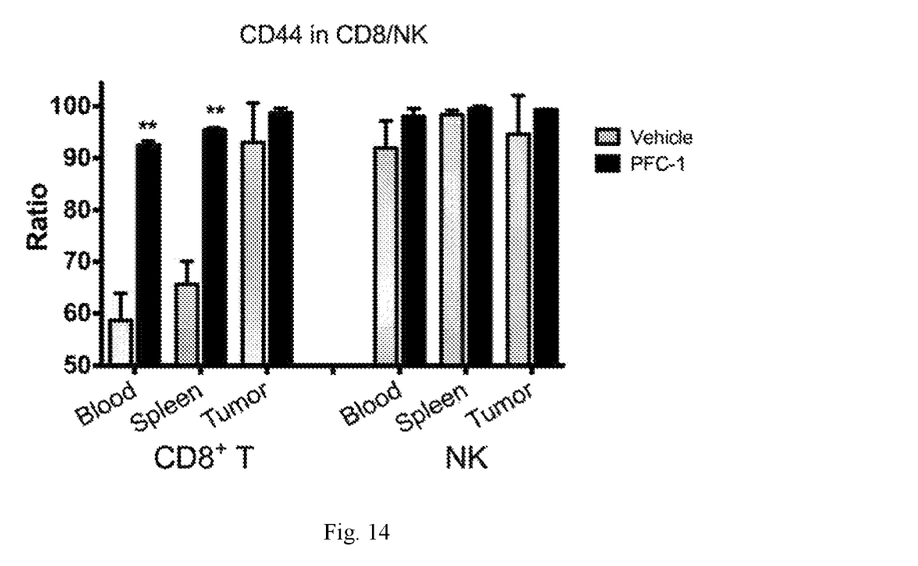
FIG. 14 shows the phenotype change of CD44 antigen on the surfaces of CD8+ T cells and NK cells of the mice received PFC-1 treatment in FIG. 10 by flow cytometry. Results represented at least three independent experiments (n=5-8 for each group). T-test was used for statistical analysis,  represents $p<0.01$, * represents $p<0.005$.

Flow cytometry was performed to analyze lymphocytes isolated from the peripheral blood, spleen and tumors of mice treated with PFC-1 or the vehicle groups. A steep increase in the number of CD8$^+$T cells was observed in the peripheral blood, spleen and tumors of mice treated with PFC-1 (FIG. 12). A significant increase in CD44, a T cell activation marker, on CD8$^+$T cells was also observed in peripheral blood, splenocytes, and tumor-infiltrating lymphocytes, suggesting that PFC-1 not only increased the population but also activated CD8$^+$T cells. PFC-1 was also able to mobilize more NK cells in tumors (FIG. 13). All of the data suggest that PFC-1 stimulate immune cells to kill tumor cells.

PFC-1 Blocks B16 Tumor Metastasis in Mouse $5\times10^5$ B16F10 melanoma cells was injected via tail vein to inoculate 4-6-week female C57BL/6 mice. Lung metastasis developed rapidly in these mice. On day 2, a single dosage of 10 µg PFC-1 or equal volume of vehicle was administered. On day 21, the mice were sacrificed and the lungs were removed, washed thoroughly with PBS and fixed in 10% formaldehyde. The metastasis nodes were counted under binocular microscope (Leica M125).

Figure 15:
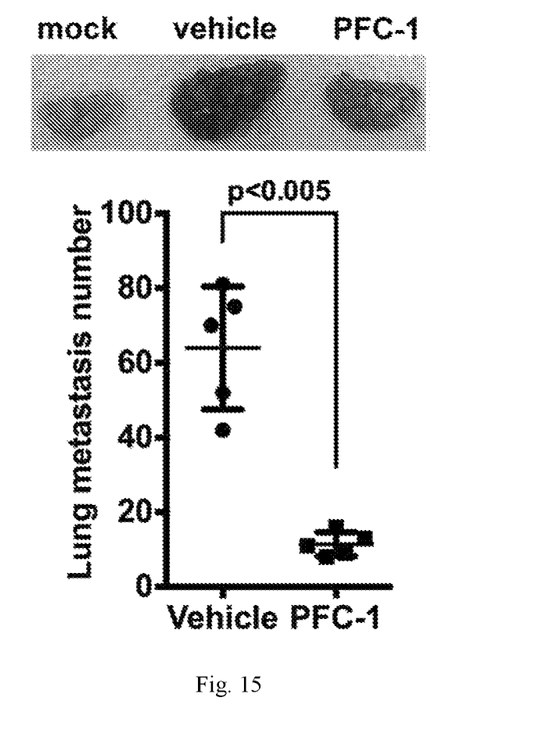
FIG. 15 shows the prevention of malignant migration of the fusion protein PFC-1 in C57BL/6 mouse. On day 0, C57BL/6 mice were injected with $5*10^5$ B16F10 mouse melanoma cells via tail vein and received 10 μg PFC-1 or 200 μl PBS on the same day via tail vein. On day 21, the mice were euthanased and lungs were removed for assessments of the severity and number of pulmonary malignant tumor under binocular microscope. The top shows the lung of a presentative mouse. Mock, not received tumor cell injection; Vehicle, control received tumor cell injection; PFC-1, received PFC-1 injection. Results were expressed as mean±SD (n=5 for each group). T-test was used for statistical analysis.

Results showed that a single intraperitoneal administration of 10 µg PFC-1 effectively reduced the average lung metastasis node number from 61, the average in the vehicle group, to 11.4 in the treated group, a decrease of more than 80% (FIG. 15), suggesting that PFC-1 can effectively block tumor metastasis.

The present technology illustratively described herein may suitably be practiced in the absence of any element or elements, limitation or limitations, not specifically disclosed herein. It should be understood that the materials, methods, and examples provided here are representative of preferred aspects, are exemplary, and are not intended as limitations on the scope of the present technology.

The invention claimed is:

1. A fusion protein, comprising at least an IL-15 peptide, and an IL-15Rα peptide, wherein the IL-15Rα peptide has a deletion of the cysteine residue at the position that precedes SEQ ID NO:2 as in a full-length IL-15Rα.

2. The fusion protein of claim 1, wherein the IL-15 peptide and the IL-15Rα peptide are arranged from the N-terminus to the C-terminus in the fusion protein.

3. The fusion protein of claim 1, further comprising an Fc domain.

4. The fusion protein of claim 1, wherein the IL-15Rα peptide comprises the amino acid sequence of SEQ ID NO:2.

5. The fusion protein of claim 1, wherein the IL-15 peptide comprises the amino acid sequence of SEQ ID NO:3.

6. A pharmaceutical composition comprising the fusion protein of claim 1, and a pharmaceutically acceptable excipient.

7. A pharmaceutical composition comprising the fusion protein of claim 1, and a further anti-tumor agent.

* * * * *